United States Patent [19]

Esanu

[11] 4,131,617

[45] Dec. 26, 1978

[54] PREPARATION OF NEW ISOBUTYLRAMIDE DERIVATIVES

[75] Inventor: André Esanu, Paris, France

[73] Assignee: Societe d'Etudes de Produits Chimiques, Paris, France

[21] Appl. No.: 778,724

[22] Filed: Mar. 17, 1977

[30] Foreign Application Priority Data

Mar. 17, 1976 [GB] United Kingdom ............... 10634/76

[51] Int. Cl.$^2$ .......................................... C07C 121/78
[52] U.S. Cl. ............................................... 260/465 D
[58] Field of Search ..................................... 260/465 D

[56] References Cited

U.S. PATENT DOCUMENTS 3,439,018  4/1969  Brookes et al. ............. 260/465 D X Primary Examiner—Dolph H. Torrence
Attorney, Agent, or Firm—Eyre, Mann, Lucas & Just

[57] ABSTRACT

A process for the preparation of an isobutyramide is disclosed. A sodium phenolate is prepared by reacting sodium with a phenol in ethanol, an excess of toluene is added to the solution to form an ethanol/toluene azeotrope which azeotrope is then removed by distillation whereafter a N-cyanoalkyl α-bromo-isobutyramide is added, the mixture is refluxed for a period of 6–15 hours after which water is added to form a precipitate which is then removed from the reaction mixture.

2 Claims, No Drawings

PREPARATION OF NEW ISOBUTYLRAMIDE DERIVATIVES

This invention relates to a process for the preparation of the new isobutyramides and their acid addition salts which are the subject of our Patent Application filed herewith and assigned Serial No. 778,729 on its filing date of March 17, 1977. The isobutyramides have the following general formula.

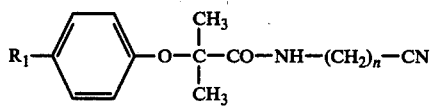

wherein $R_1$ represents a halogen atom and n is an integer from 2 to 6.

The above compounds may be prepared according to this invention by the action of the corresponding substituted sodium phenolate of the formula I, a non polar solvent.

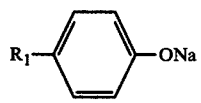

on the appropriate N-cyanoalkyl α-bromo-isobutyramide II

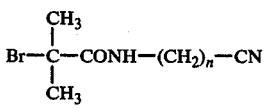

in which $R_1$ and n are as above defined.

The N-cyanoalkyl α-bromo-isobutyramide II may be readily obtained from α-bromo-isobutyryl chloride on the appropriate aminoalkyl nitrile according to the reation scheme:

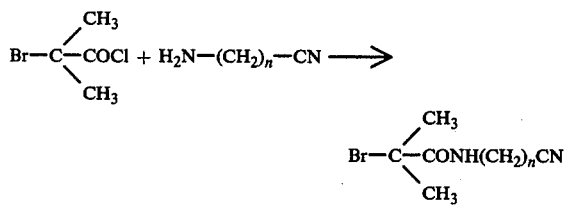

Preferably the synthesis commences with the appropriate substituted phenol which is converted into the sodium phenate I by reaction with sodium in solution in ethanol. The ethanol is then replaced by toluene by the addition of an excess of toluene and subsequent distillation of the azeotrope.

To the solution in toluene is added the N-cyanoalkyl α-bromo-isobutyramide II and the reaction mixture is preferably refluxed for from 6 to 15 hours.

This invention is illustrated by the following Examples.

EXAMPLE 1:

N-cyanoethyl p-chlorophenoxy isobutyramide

Into a 25 liter reactor fitted with cooling and stirring means there were poured 3 liters of ethanol, 60 g of sodium and 250 g of p-chlorophenol (1.944 mol). After stirring for 1 hour there were added 3 liters of toluene and the ethanol/toluene azeotrope was removed by distillation; 2 more liters of toluene were added and also 425 g of N-cyanoethyl α-bromo-isobutyramide, (1.944 mol).

The mixture was refluxed for 10 hours, and 2 liters of toluene were then removed by distillation. The resulting mixture was treated with water which gave a precipitate which was separated, washed with water, made acid with HCl until is was neutral, dried and crystallized from di-isopropylether.

There were thus obtained 348 g (yield 67%) of a white crystalline product melting at 71° C. The composition of the product corresponded to the fomula $C_{13}H_{15}O_2N_2Cl$ (molecular weight 266.72). The compound was insoluble in water but soluble in most common organic solvents.

EXAMPLE 2:

N-cyanoethyl p-fluorophenoxy isobutyramide

The procedure of Example 1 was repeated except that the p-chlorophenol was replaced by p-fluorophenol, which after the dodium treatment was reacted with N-Cyanoethyl α-bromo-isobutyramide.

There was thus obtained, with a yield of 67% a white crystalline product melting at 75° C. The analysis shows a good correspondence with the formula $C_{15}H_{15}O_2N_2$ (molecular weight 250.2).

EXAMPLE 3:

N-cyanobutyl p-chlorophenoxy isobutyramide

The procedure of example 1 was repeated exept that N-Cyanoethyl α-bromo-isobutyramide was replaced by N-Cyanobutyl α-bromo-isobutyramide; yield 87% of a white crystalline product melting at 88° C. the analysis of which shows a good correspondence with the formula $C_{15}H_{19}N_2O_2Cl$.

I claim:

1. A process for the preparation of an isobutyramide of the formula

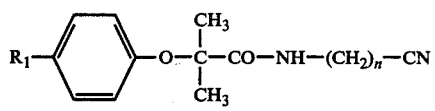

wherein:
$R_1$ is a halogen; and
n is an integer from 2 to 6 said process comprising:
(a) forming a sodium phenolate by reacting in ethanol sodium with a phenol of the formula

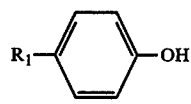

wherein $R_1$ is a halogen;
(b) adding an excess of toluene to the ethanol solution of sodium phenolate of step (a) whereby an ethanol/toluene azeotrope is formed;
(c) removing the azeotrope of step (b) by distillation;
(d) forming a reaction mixture by adding to the solution of sodium phenolate in toluene remaining from step (c) an N-cyanoalkyl α-bromo-isobutyramide of the formula:

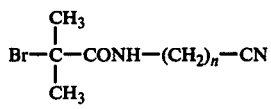

wherein n is an integer from 2 to 6;

(e) refluxing the reaction mixture of step (d) for a period of from 6 to 15 hours;
(f) adding water to the refluxed reaction mixture whereby a precipitate is formed in the reaction mixture; and
(g) separating the precipitate of step (f) from the reaction mixture.

2. The process of claim 1 further including the following additional steps: (a) neutralizing the separated precipitate by addition of acid until a neutral pH is obtained; and (b) drying the neutralized precipitate.

* * * * *